(12) United States Patent
Cherpeck et al.

(10) Patent No.: US 7,285,518 B2
(45) Date of Patent: Oct. 23, 2007

(54) DIBENZO[B]PERHYDROHETEROCYCLIC AMINES AND LUBRICATING OIL COMPOSITIONS

(75) Inventors: Richard E. Cherpeck, Cotati, CA (US); Carrie Y. Chan, Daly City, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 11/316,099

(22) Filed: Dec. 21, 2005

(65) Prior Publication Data

US 2007/0142245 A1    Jun. 21, 2007

(51) Int. Cl.
*C10M 133/40* (2006.01)
*C10M 133/44* (2006.01)
*C10M 133/48* (2006.01)
*C07D 221/04* (2006.01)
*C07D 417/12* (2006.01)
*C07D 263/58* (2006.01)
*C07D 235/30* (2006.01)
*C07D 307/82* (2006.01)

(52) U.S. Cl. ............... 508/266; 508/269; 508/270; 508/271; 546/112; 548/159; 548/217; 548/305.1; 549/434; 549/462

(58) Field of Classification Search ............... 546/112; 548/159, 217, 305.1; 549/434, 462; 508/266, 508/269, 270, 271

See application file for complete search history.

(56) References Cited

U.S. PATENT DOCUMENTS

| | | |
|---|---|---|
| 1,896,461 A | 2/1933 | Muth |
| 2,342,135 A | 2/1944 | Gibbs |
| 2,365,018 A | 12/1944 | Gibbs |
| 2,718,501 A | 9/1955 | Harle |
| 2,794,020 A | 5/1957 | Harris et al. |
| 2,943,112 A | 6/1960 | Popoff et al. |
| 2,958,663 A | 11/1960 | Westcott et al. |
| 2,998,468 A | 8/1961 | Wilde |
| 3,345,992 A | 10/1967 | Lederman et al. |
| 3,362,929 A | 1/1968 | Kehe |
| 3,452,056 A | 6/1969 | Sundholm |
| 3,480,635 A | 11/1969 | Altwicker |
| 3,505,225 A | 4/1970 | Wheeler |
| 3,533,992 A | 10/1970 | Sundholm |
| 3,655,559 A | 4/1972 | Holt |
| 3,660,290 A | 5/1972 | Schlobohm |
| 3,910,918 A | 10/1975 | Monroy |
| 3,944,492 A | 3/1976 | Wheeler |
| 4,069,195 A | 1/1978 | Layer et al. |
| 4,089,792 A | 5/1978 | Lowe |
| 4,692,258 A | 9/1987 | Rasberger et al. |
| 4,828,741 A | 5/1989 | Meier et al. |
| 4,929,732 A | 5/1990 | Meier et al. |
| 4,965,006 A | 10/1990 | Meier et al. |
| 5,198,134 A | 3/1993 | Steinberg et al. |
| 5,232,614 A | 8/1993 | Colclough et al. |
| 5,246,606 A | 9/1993 | Evans |
| 5,310,491 A | 5/1994 | Downs et al. |
| 5,420,354 A | 5/1995 | Malz et al. |
| 5,451,702 A | 9/1995 | Stern et al. |
| 5,595,963 A | 1/1997 | Puckace et al. |
| 5,834,544 A | 11/1998 | Lin et al. |
| 6,121,209 A | 9/2000 | Watts et al. |
| 6,174,842 B1 | 1/2001 | Gatto et al. |
| 6,315,925 B1 | 11/2001 | Aebli et al. |
| 6,426,324 B1 | 7/2002 | Lai et al. |
| 6,806,241 B2 | 10/2004 | Karol et al. |
| 6,939,969 B2 * | 9/2005 | Peters et al. ............... 546/171 |

OTHER PUBLICATIONS

McQueen, J.S. et al., Friction and wear of tribofilms formed by zinc dialkyl dithiophosphate antiwear additive in low viscosity engine oils, Elsevier Science Ltd., Tribology International 38, (2005), pp. 289-297.

Ingold, K.U., Inhibition of the Autoxidation of Organic Substances in the Liquid Phase. Division of Applied Chemistry, National Research Council Publication No. 6537, American Chemical Society, Chemical Reviews, vol. 61, (1961), pp. 563-589.

Nishiyama, Tomihiro et al., Antioxidant activity of the fused heterocyclic compounds, 1,2,3,4-tetrahydroquinolines, and related compounds-effect of *ortho*-substituents, Elsevier Science Ltd., Polymer Degradation and Stability 79, (2003), pp. 225-230.

Dorey, Gilbert et al., New Quinolinic Derivatives as Centrally Active Antioxidants, Elsevier Science Ltd., Bioorganic & Medicinal Chemistry Letters 10, (2000), pp. 935-939.

Denisov, Evgeniy T. et al., Mechanisms of Action and Reactivities of the Free Radicals of inhibitors, American Chemical Society, Chemical Reviews, vol. 87, No. 6 (1987), pp. 1313-1357.

Nishiyama, Tomihiro et al., Antioxidant activity of aromatic cyclic amine derivatives, Elsevier Science Ltd., Polymer Degradation and Stability 75, (2002), pp. 549-554.

\* cited by examiner

*Primary Examiner*—Kamal A. Saeed
*Assistant Examiner*—Karen Cheng
(74) *Attorney, Agent, or Firm*—Joseph P. Foley; Claude J. Caroli

(57) ABSTRACT

Dibenzo[b]perhydroheterocyclic amine compounds have shown to be particularly useful as stabilizers. The compounds may serve as antioxidants, antiozoants, heat stabilizers and ultraviolet light stabilizers and such compounds are oil soluble, thus particularly suited for use as an antioxidant in a lubricating oil composition.

22 Claims, No Drawings

DIBENZO[B]PERHYDROHETEROCYCLIC AMINES AND LUBRICATING OIL COMPOSITIONS

FIELD OF THE INVENTON

Dibenzo[b]perhydroheterocyclic amines compounds have demonstrated utility in mitigating oxidation in functional fluids. Accordingly, the present invention is directed to substituted and unsubstituted dibenzo[b]perhydroheterocyclic amines compounds and lubricating compositions containing such.

BACKGROUND OF THE INVENTION

Diarylamine antioxidants are known and have been widely used to improve the thermal-oxidative stability and/or light induced degradation in numerous products used in engineering; for example, they can improve the performance properties in lubricants, hydraulic fluids, metal working fluids, fuels or polymers, just to name a few.

Commonly, these diarylamines have been alkylated, see for example, U.S. Pat. No. 2,943,112 which discloses an improved process for alkylating diphenylamine and U.S. Pat. No. 3,655,559 which discloses alkylated diphenylamines as stabilizers. Alkaryl substituted diphenylamines and phenylnapthylamines (such as α-methylstyryl-diphenylamine) are disclosed for example in U.S. Pat. Nos. 3,533,992; 3,452,056 and 3,660,290. Substittued paraphenylene diamines have also been disclosed as antioxidants for lubricants in which iron-catalyzed oxidation reaction can occur, see U.S. Pat. No 5,232,614.

Additionally, alkyl substituted 1,2-dihydroquinoline and polymers thereof, have been employed as antioxidants, see U.S. Pat. No. 3,910,918. While, U.S. Pat. No. 5,310,491 discloses the reaction product of an alkyl substituted 1,2-dihydroquinoline with a diarylamine. Tetrahydroquinones and substituted tetrahydroquinones have also have also been disclosed as antioxidants, see for example U.S. Pat. Nos. 2,794,020; 3,362,929; 4,692,258 and 4,965,006. Likewise decahydroquinolines and substituted decahydroquinolines have been employed as antioxidants, see U.S. Pat. Nos. 2,998,468 and 4,069,195.

In order to satisfy the more severe operating conditions and new applications which require improved oxidation inhibition, continued development of new compounds to mitigate oxidation is of paramount interest. The compounds of the present invention demonstrate superior performance in an organic substrate and thus may serve the continued need.

SUMMARY OF THE INVENTION

The present invention is directed in part to compounds which may serve as antioxidants, antiozoants, heat stabilizers and ultraviolet light stabilizers and such compounds are oil soluble, thus particularly suited for use as an antioxidant in a lubricating oil composition. Accordingly, the present invention discloses a compound according to formula I:

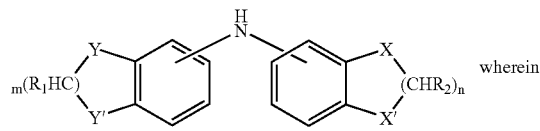

Formula I wherein $R_1$ and $R_2$ are each independently selected from hydrogen and alkyl from 1 to 20 carbon atoms; X and X' are independently selected from —$CHR_3$—, oxygen, sulfur or $NR_4$, wherein $R_3$ and $R_4$ are independently hydrogen or alkyl from 1 to 6 carbon atoms, with the proviso that at least one of X or X' is a heteroatom positioned ortho or para to the bridging ring nitrogen; and Y and Y' are independently selected from —$CHR_5$—, oxygen, sulfur or $NR_6$ wherein $R_5$ and $R_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

Each benzo[b]perhydroheterocyclic ring can contain one or two heteroatoms, thus the compound can contain two, three or four heteroatoms. Thus for example if X and Y are the heteroatoms, they can be selected from group Z (N,N; N,O; N,S; O,O; O,S and S,S). Alternatively, X and X' may be the heteroatoms of group Z and Y may be a single heteroatom selected from N, O, or S; or X, X' and Y,Y' may each be independently selected from group Z. Particularly preferred heteroatoms are nitrogen and oxygen, and mixtures thereof.

Therefore in one aspect, at least one of X and X' is oxygen or $NR_4$, where $R_4$ is hydrogen or alkyl from 1 to 6 carbon atoms, the heterocycle may contain a single heteroatom; thus one of X or X' is $CHR_3$—, and be unsubstituted or alkyl substituted with from one to 6 carbon atoms. In this regard preferable each $R_2$ is hydrogen. In the above aspect, it is also preferred that at least one of Y and Y' is oxygen or $NR_6$, where $R_6$ is hydrogen or alkyl from 1 to 6 carbon atoms and in this regard preferable each $R_1$ is hydrogen. Even more preferably, at least one of Y and Y' is —$CHR_5$— with —$CH_2$— being particularly preferred.

Each benzo[b]perhydroheterocyclic ring can contain a five or six membered heterocycle. The heterocyclic rings may be the same size and can have the same heteroatoms. In this aspect for example, m is equal to n, and more specifically they are both one, and preferred are when X and Y are oxygen and moreover wherein X' and Y' are independently oxygen or —$CH_2$—.

In another aspect, X and X' are independently selected from —$CHR_3$— and $NR_4$ wherein $R_3$ and $R_4$ are independently hydrogen or alkyl from 1 to 6 carbon atoms. Particularly preferred compounds are defined when both m and n are two. Moreover preferably in this aspect, Y and Y' are independently selected from —$CHR_5$— and $NR_6$ wherein $R_5$ and $R_6$ are independently hydrogen or alkyl from 1 to 6 carbon atoms. With unsubstitiuted compounds being particularly preferred.

Other preferred compounds of the present invention are defined in part by the examples, thus particularly preferred compounds of Formula I are selected from unsubstituted and alkyl substituted with from one to six carbon atoms with the group consisting of: N-quinolin-8-ylquinolin-6-amine; N-(1,2,3,4-tetrahydroquinolin-8-yl)-1,2,3,4-tetrahydroquinolin-6-amine; N-(2,3-dihydro-1-benzofuran-5-yl)-2,3-dihydro-1-benzofuran-5-amine; N-1,3-benzodioxol-5-yl-1,3-benzodioxol-5-amine.

The present invention is further directed to lubricating compositions comprising an oil of lubricating viscosity and a compound of the present invention. Preferably the lubricating oil is present in a major amount and the composition contains a minor amount of the compound of the present invention. More particularly, the composition contains an antioxidant effective amount of the compound of the present invention. The lubricating composition can comprise further additives for their intended use, such as detergents, dispersants, additional antioxidants, antiwear agents, friction modifiers, etc. In yet another aspect, the present invention is directed to a method for improving the oxidation inhibition of an organic substrate by adding an effective amount of the compound of the present invention.

DETAILED DESCRIPTION OF THE INVENTION

Inhibition of free radical-mediated oxidation is one of the most important reactions in organic substrates and is commonly used in rubbers, polymers and lubrication oils; namely, since these chemical products may undergo oxidative damage by the autoxidation process. Hydrocarbon oxidation is a three step process which comprises: initiation, propagation and termination. Oxidative degradation and the reaction mechanisms are dependent upon the specific hydrocarbons, temperatures, operating conditions, catalysts such as metals, etc., which more detail can be found in Chapter 4 of Mortier R. M. et al., 1992, "Chemistry and Technology of Lubricants Initiation", VCH Publishers, Inc.; incorporated herein by reference in its entirety. Initiation involves the reaction of oxygen or nitrogen oxides (NO$_x$) on a hydrocarbon molecule. Typically, initiation starts by the abstraction of hydrocarbon proton. This may result in the formation of hydrogen peroxide (HOOH) and radicals such as alkyl radicals (R.) and peroxy radicals (ROO.). During the propagation stage, hydroperoxides may decompose, either on their own or in the presence of catalysts such as metal ions, to alkoxy radicals (RO.) and peroxy radicals. These radicals can react with the hydrocarbons to form a variety of additional radicals and reactive oxygen containing compounds such as alcohols, aldehydes, ketones and carboxylic acids; which again can further polymerize or continue chain propagation. Termination results from the self termination of radicals or by reacting with oxidation inhibitors.

The uncatalyzed oxidation of hydrocarbons at temperatures of up to about 120° C. primarily leads to alkyl-hydroperoxides, dialkylperoxides, alcohols, ketones; as well as the products which result from cleavage of dihydroperoxides such as diketones, keto-aldehydes hydroxyketones and so forth. At higher temperatures (above 120° C.) the reaction rates are increased and cleavage of the hydroperoxides plays a more important role. Additionally, at the higher temperatures, the viscosity of the bulk medium increases as a result of the polycondesation of the difunctional oxgenated products formed in the primary oxidation phase. Further polycondesation and polymerization reaction of these high molecular weight intermediates results in products which are no longer soluble in the hydrocarbon and form varnish like deposits and sludge.

Since autoxidation is a free-radical chain reaction, it therefore, can be inhibited at the initiation and/or propagation steps. Typical oxidation inhibition by diarylamines, such as dialkyldiphenylamine and N-phenyl-α-napthylamine, also involves radical scavenging. The transfer of hydrogen from the NH group of the amine to the peroxide radicals results in the formation of a diarylamino radical which is resonance stabilized, thus prevents new chains from forming. A secondary peroxy radical or hydroperoxide can react with the diarylamino radical to form the nitroxy radical, which is also a very potent inhibitor. Increased demands have been placed on many functional fluids which have in-turn placed emphasis on new inhibitors.

The present invention is directed in part to aryl-amino bridged dibenzo[b]perhydroheterocyclic compounds particularly useful as stabilizers. The compounds may serve as antioxidants, antiozoants, heat stabilizers and ultraviolet light stabilizers and such compounds are oil soluble, thus particularly suited for use an antioxidant in a lubricating oil composition. Disclosed are particularly suited resonance stabilized inhibitor compounds according to formula I:

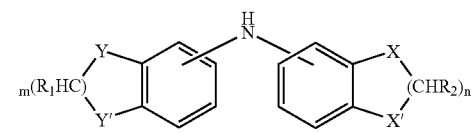

Formula I wherein R$_1$ and R$_2$ are each independently selected from hydrogen and alkyl from 1 to 20 carbon atoms; X and X' are independently selected from —CHR$_3$—, oxygen, sulfur or NR$_4$, wherein R$_3$ and R$_4$ are independently hydrogen or alkyl from 1 to 6 carbon atoms, with the proviso that at least one of X or X' is a heteroatom positioned ortho or para to the bridging ring nitrogen; and Y and Y' are independently selected from —CHR$_5$—, oxygen, sulfur or NR$_6$ wherein R$_5$ and R$_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

Improved oil solubility and resonance stabilization may be accomplished by alkyl substitution on the heterocyclic ring. Thus in one aspect, at least one heterocyclic ring is alkyl substituted. Preferred substituents are at R$_1$ or R$_2$, or when present R$_3$ or R$_4$.

Oil solubility is dependent upon the type and degree of heteroatom content in the compound, thus alkyl substitution may be optional when X' and Y' are not heteroatoms. With increasing the heteroatoms in the compound, for example if X, X', Y and Y' are nitrogen, then preferably at least one alkyl substituent can be imparted for oil solubility. Thus one embodiment of the invention is directed to oil soluble compounds of Formula I and lubricating oil compositions containing such.

An aspect of the present invention is directed to where X' and Y' are —CHR$_3$— and —CHR$_5$— respectively. In this regard, preferably at least one X or Y is selected to have a nitrogen atom or an oxygen atom, and more particularly X and Y are selected to both contain nitrogen atoms or to both contain oxygen atoms. In this aspect, X and Y selected from NR$_4$ and NR$_6$ although each heterocyclic ring may have different substituent groups; or X and Y are both oxygen.

By way of an example, when X and Y are selected to be the heteroatoms, the othro/ortho and para/para positions of X and Y to the bridging ring nitrogen atom are depicted below. As is evident, otho/para and para/ortho are contemplated.

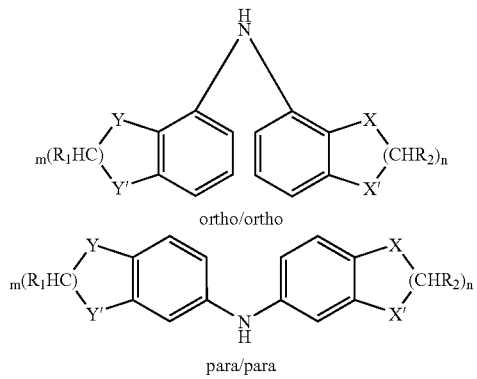

ortho/ortho para/para

Particularly robust properties have been demonstrated for oxygen and nitrogen heterocycles. Thus particularly preferred compounds of formula I are depicted when X and Y are selected from oxygen, —NH— and —N(alkyl from 1 to 6 carbon atoms)-. Therefore, particularly suited fused ring benzo[b]perhydroheterocylic moieties include substituted and unsubstituted: 2,3-dihydro-indole, 2,3-dihydro-benzofuran, 2,3-dihydro-benzoimidazole, 2,3dihydro-benzooxaole, 2,3-dihydro-benzothiazole, benzo[1,3]oxathiole and benzo[1,3]dioxole; as well as the larger substituted and unsubstituted heterocyclic rings consisting of the group: 1,2,3,4-tetrahydroquinoline; 1,2,3,4-tetrahydroqinoxaline; 3,4-dihydro-2H-benzo[1,4]thiazine; 3,4-dihydro-2H-benzo[1,4]oxazine; 2,3-dihydro-benzo[1,4]oxathiine; 2,3-dihydro-benzo[1,4]dioxine and chroman. Particularly preferred perhydroheterocylic moieties are selected so that X' and Y' are —CH— or —C(alkyl from 1 to 6 carbon atoms) and thus the substituted and unsubstituted perhydroheterocylic moieties selected from the group consisting of 2,3,-dihydrobenzofuran, benzo[1,3]dioxole and 1,2,3,4-tetrahydroquinoline.

One aspect of the invention is characterized by compounds of Formula II

Formula II

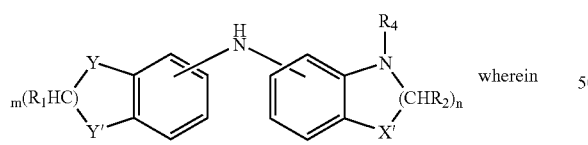

wherein $R_1$ and $R_2$ are each independently selected from hydrogen and alkyl from 1 to 20 carbon atoms; X' is selected from —$CHR_3$—, oxygen, sulfur or $NR_4$, wherein $R_3$ and each $R_4$ are independently hydrogen or alkyl from 1 to 6 carbon atoms, with the proviso that at least one heteroatom in the ring defined along with X' is attached at a position ortho or para to the bridging ring nitrogen; and Y and Y' are independently selected from —$CHR_5$—, oxygen, sulfur or $NR_6$ wherein $R_5$ and $R_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

Improved oil solubility and resonance stabilization may be accomplished by alkyl substitution on the heterocyclic ring. Alkyl substitituents have an increasing importance with regard to the degree of heteroatoms in the compound. Thus in one aspect, at least one heterocyclic ring is alkyl substituted. Preferred substituents are at $R_1$ or $R_2$, or when present $R_3$ or $R_4$. Thus in one aspect, $R_3$ and $R_4$ are hydrogen.

In one aspect, performance has demonstrated improved results when the heteroatom is nitrogen, which in some regard has shown improvement over oxygen of which, both are thought to be better than sulfur. Thus another aspect is directed to the compounds of Formula II wherein X', Y and Y' are independently selected from —$CH_2$—, —CH(alk)-, oxygen, —NH—, or N(alk) where alk is alkyl from one to six carbon atoms. More preferred is wherein X', Y and Y' are independently selected from —$CH_2$—, oxygen or —NH— group. In the above particularly preferred compounds are m=n and moreover when m=2. In this aspect particularly preferred compounds are defined when $R_1$ and $R_2$ are hydrogen.

A subset of compounds contain at least two nitrogen heteroatoms is characterized by Formula IIa:

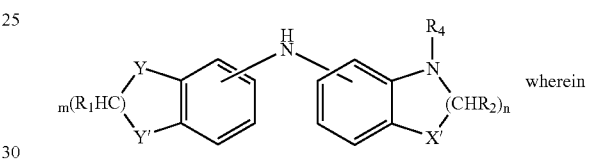

wherein $R_1$ and $R_2$ are each independently selected from hydrogen and alkyl from 1 to 20 carbon atoms; X' is selected from —$CHR_3$—, oxygen, sulfur or $NR_4$, wherein $R_3$ and each $R_4$ are independently hydrogen or alkyl from 1 to 6 carbon atoms, with the proviso that at least one heteroatom in the ring defined along with X' is attached at a position ortho or para to the bridging ring nitrogen; and Y' is selected from —$CHR_5$—, oxygen, sulfur or $NR_6$ wherein $R_5$ and $R_6$ are independently hydrogen or alkyl from 1 to 6 carbon atoms; with the proviso that at least one heteroatom in the ring defined along with Y' is attached at a position ortho or para to the bridging ring nitrogen; and m and n are independently integers from 1 to 2.

Another aspect of the invention is characterized by compounds of Formula III

Formula III

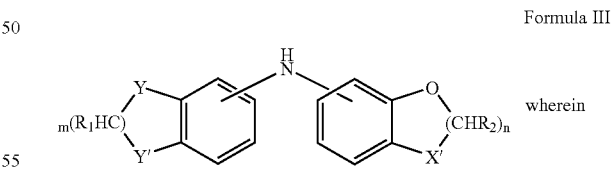

wherein $R_1$ and $R_2$ are each independently selected from hydrogen and alkyl from 1 to 20 carbon atoms; X' is selected from —$CHR_3$—, oxygen, sulfur or $NR_4$, wherein $R_3$ and $R_4$ are independently hydrogen or alkyl from 1 to 6 carbon atoms, with the proviso that at least one heteroatom in the ring defined along with X' is attached at a position ortho or para to the bridging ring nitrogen; and Y and Y' are independently selected from —$CHR_5$—, oxygen, sulfur or $NR_6$ wherein $R_5$ and $R_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

Improved oil solubility and resonance stabilization may be accomplished by alkyl substitution on the heterocyclic ring. Alkyl substitituents have an increasing importance with regard to the degree of heteroatoms in the compound. Thus in one aspect, at least one heterocyclic ring is alkyl substituted. Preferred substituents are at $R_1$ or $R_2$, or when present $R_3$ or $R_4$. Thus in one aspect, $R_3$ and $R_4$ are hydrogen.

In one aspect, performance has demonstrated improved results when the heteroatom is nitrogen, which in some regard has shown improvement over oxygen of which, both are thought to be better than sulfur. Thus another aspect is directed to the compounds of Formula III wherein X', Y and Y' are independently selected from —$CH_2$—, —CH(alk)-, oxygen, —NH—, or N(alk) where alk is alkyl from one to six carbon atoms. More preferred is wherein X', Y and Y' are independently selected from —$CH_2$—, oxygen or —NH— group. In the above particularly preferred compounds are m=n and moreover when m=1, such intermediates are readily commercially available. In this aspect particularly preferred compounds are defined when $R_1$ and $R_2$ are hydrogen.

The compounds of Formula I are particularly useful when employed in a lubricating composition comprising the compound of Formula I with an oil of lubricating viscosity.

The lubricant compositions of this invention include a major amount of base oil of lubricating viscosity. Base Oil as used herein is defined as a base stock or blend of base stocks which is a lubricant component that is produced by a single manufacturer to the same specifications (independent of feed source or manufacturer's location): that meets the same manufacturer's specification; and that is identified by a unique formula, product identification number, or both. Base stocks may be manufactured using a variety of different processes including but not limited to distillation, solvent refining, hydrogen processing, oligomerization, esterification, and rerefining. Rerefined stock shall be substantially free from materials introduced through manufacturing, contamination, or previous use. The base oil of this invention may be any natural or synthetic lubricating base oil fraction particularly those having a kinematic viscosity at 100 degrees Centigrade (C) and about 5 centistokes (cSt) to about 20 cSt, preferably about 7 cSt to about 16 cSt, more preferably about 9 cSt to about 15 cSt. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. A preferred base oil is one that comprises little, if any, heavy fraction; e.g., little, if any, lube oil fraction of viscosity 20 cSt or higher at 100 degrees C.

The base oil may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Saturates levels and viscosity indices for Group I, II and III base oils are listed in Table 1. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

TABLE 1

Saturates, Sulfur and Viscosity Index of Group I, II and III Base Stocks

| Group | Saturates (As determined by ASTM D 2007) Sulfur (As determined by ASTM D 2270) | Viscosity Index (As determined by ASTM D 4294, ASTM D 4297 or ASTM D 3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and interpolymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers. Tri-alkyl phosphate ester oils such as those exemplified by tri-n-butyl phosphate and tri-iso-butyl phosphate are also suitable for use as base oils.

Silicon-based oils (such as the polyakyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The base oil may be derived from unrefined, refined, rerefined oils, or mixtures thereof. Unrefined oils are obtained directly from a natural source or synthetic source (e.g., coal, shale, or tar sand bitumen) without further purification or treatment. Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Base oil derived from the hydroisomerization of wax may also be used, either alone or in combination with the aforesaid natural and/or synthetic base oil. Such wax isomerate oil is produced by the hydroisomerization of natural or synthetic waxes or mixtures thereof over a hydroisomerization catalyst.

It is preferred to use a major amount of base oil in the lubricating oil of this invention. A major amount of base oil as defined herein comprises 40 wt. % or more. Preferred amounts of base oil comprise about 40 wt. % to about 97 wt. % of at least one of Group II, III and IV base oil or preferably greater than about 50 wt. % to about 97 wt. % of at least one of Group II, III and IV base oil or more preferably about 60 wt. % to about 97 wt. % of at least one of Group II, III and IV base oil. (When wt. % is used herein, it is referring to wt. % of the lubricating oil unless otherwise specified.) A more preferred embodiment of this invention may comprise an amount of base oil that comprises about 85 wt. % to about 95 wt. % of the lubricating oil.

The amount of dibenzo[b]perhydroheterocyclic amine compounds of the present invention in the lubricating oil composition will be in a minor amount compared to the base oil of lubricating viscosity. Generally, it will be in an amount from about 0.01 to 10 wt %, preferably from about 0.1 to about 2.0 wt %, more preferably from about 0.3 to about 1.8 wt % and even more preferably from about 0.5 to about 1.5 wt %, based on the total weight of the lubricating oil composition.

The following additive components are examples of components that can be favorably employed in combination with the lubricating additive of the present invention. These examples of additives are provided to illustrate the present invention, but they are not intended to limit it.

(A) Ashless dispersants: alkenyl succinimides, alkenyl succinimides modified with other organic compounds such as ethylene carbonate, polysuccinimides, and alkenyl succinimides modified with boric acid, alkenyl succinic ester.

(B) Oxidation inhibitors:

1) Phenol type phenolic oxidation inhibitors: 4,4'-methylenebis(2,6-di-tert-butylphenol), 4,4'-bis(2,6-di-tert-butylphenol), 4,4'-bis(2-methyl-6-tert-butylphenol), 2,2'-(methylenebis(4-methyl-6-tert-butyl-phenol)), 4,4'-butylidenebis(3-methyl-6-tert-butylphenol), 4,4'-isopropylidenebis(2,6-di-tert-butylphenol), 2,2'-methylenebis(4-methyl-6-nonylphenol), 2,2'-isobutylidene-bis(4,6-dimethylphenol), 2,2'-methylenebis(4-methyl-6-cyclohexylphenol), 2,6-di-tert-butyl4-methylphenol, 2,6-di-tert-butyl4-ethylphenol, 2,4-dimethyl-6-tert-butyl-phenol, 2,6-di-tert-α-dimethylamino-p-cresol, 2,6-di-tert-4(N, N'dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-butylbenzyl)-sulfide, and bis (3,5-di-tert-butyl4-hydroxybenzyl).

2) Diphenylamine type oxidation inhibitor: alkylated diphenylamine, phenyl-α-naphthylamine, and alkylated α-naphthylamine.

3) Other types: metal dithiocarbamate (e.g., zinc dithiocarbamate), and methylenebis(dibutyldithiocarbamate).

(C) Rust inhibitors (Anti-rust agents):

1) Nonionic polyoxyethylene surface active agents: polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol mono-oleate, and polyethylene glycol monooleate.

2) Other compounds: stearic acid and other fatty acids, dicarboxylic acids, metal soaps, fatty acid amine salts, metal salts of heavy sulfonic acid, partial carboxylic acid ester of polyhydric alcohol, and phosphoric ester.

(D) Demulsifiers: addition product of alkylphenol and ethyleneoxide, polyoxyethylene alkyl ether, and polyoxyethylene sorbitane ester.

(E) Extreme pressure agents (EP agents):, sulfurized oils, diphenyl sulfide, methyl trichlorostearate, chlorinated naphthalene, benzyl iodide, fluoroalkylpolysiloxane, and lead naphthenate.

(F) Friction modifiers: fatty alcohol, fatty acid, amine, borated ester, and other esters (G) Multifunctional additives: sulfurized oxymolybdenum dithiocarbamate, sulfurized oxymolybdenum organo phosphorodithioate, oxymolybdenum monoglyceride, oxymolybdenum diethylate amide, amine-molybdenum complex compound, and sulfur-containing molybdenum complex compound (H) Viscosity Index improvers: polymethacrylate type polymers, ethylene-propylene copolymers, styrene-isoprene copolymers, hydrated styrene-isoprene copolymers, polyisobutylene, and dispersant type viscosity index improvers.

(I) Pour point depressants: polymethyl methacrylate.

(K) Foam Inhibitors: alkyl methacrylate polymers and dimethyl silicone polymers.

(L) Wear inhibitors: zinc dialkyldithiophosphate (Zn-DTP, primary alkyl type & secondary alkyl type).

General Synthetic Procedures

The the dibenzo[b]perhydroheterocyclic amines of this invention may be prepared by the following general methods and procedures. It should be appreciated that where typical or preferred process conditions (e.g., reaction temperatures, times, mole ratios of reactants, solvents, pressures, etc.) are given; other process conditions may also be used unless otherwise stated. Optimum reaction conditions may vary with the particular reactants or solvents used, but such conditions can be determined by one skilled in the art by routine optimization procedures.

Those skilled in the art will also recognize that it may be necessary to block or protect certain functional groups while conducting the following synthetic procedures. In such cases, the protecting group will serve to protect the functional group from undesired reactions or to block its undesired reaction with other functional groups or with the reagents used to carry out the desired chemical transformations. The proper choice of a protecting group for a particular functional group will be readily apparent to one skilled in the art. Various protecting groups and their introduction and removal are described, for example, in T. W. Greene and P. G. M. Wuts, *Protective Groups in Organic Synthesis*, Second Edition, Wiley, New York, 1991, and references cited therein.

Synthesis

The dibenzo[b]perhydrohetocylic amines of the present invention can be prepared by the reduction of dibenzo[b] hetocylic amines as illustrated in sequence (I).

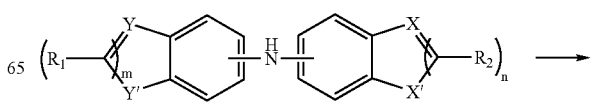

-continued

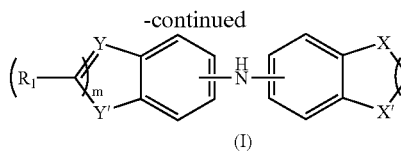

(I)

The dibenzo[b]hetocylic amines may be prepared by the reaction sequences depicted in (II) and (III)

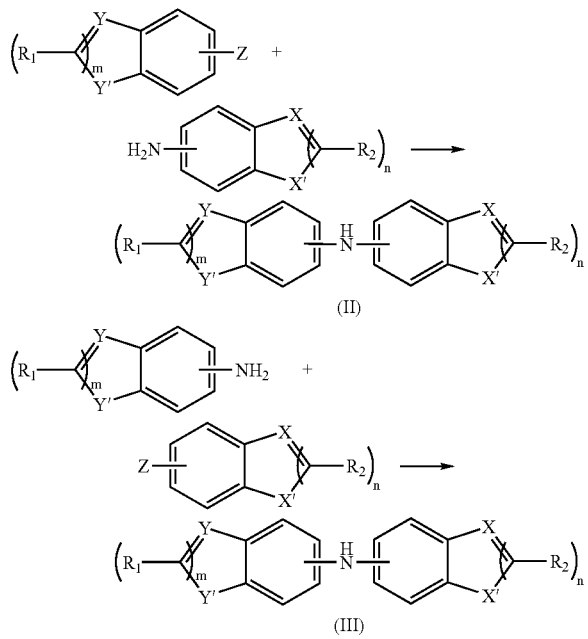

wherein $R_1$, $R_2$, m, n, X, X', Y and Y' are as defined herein and Z is —OH, —NH$_2$, Cl, Br or I.

The coupling reactions shown in (II) and (III) are known in the art for the synthesis of diphenylamines. These coupling methods are applicable to the synthesis of dibenzo[b]heterocyclic amines. Particularly noteworthy coupling reactions for the synthesis of anilinoquinolines are described by Buu-Hoi, Royer and Hubert-Habart, *J. Chem. Soc.*, 1956, 2048-2051 and Okada, Suzuki, Hirose, Toda and Ozawa, *Chem. Commun.*, 2001, 2492-2493. Buchwald and Hartwig have developed a palladium catalyzed coupling of aromatic amines and aromatic halides which is applicable to the synthesis of dibenzo[b]heterocyclic amines (Wolfe, Wagaw, Marcoux and Buchwald, *Acc. Chem. Res.*, 1998, 805-818 and references cited therein and J. C. Peters, S. B. Harkins, S. D. Brown and M. D W. Day, *Inorg. Chem.*, 2001, 40, 5083-5091). A copper catalyzed method has been developed by Patil, Kelkar, Nabi, and Chaudhari, *Chem. Commun.*, 2003, 2460-2461.

There are several methods to reduce the dibenzo[b]heterocyclic amines to dibenzo[b]perhydroheterocyclic amines. The methods that can be employed are the same as those for the reduction of quinoline to tetrahydroquinoline provided that any functionality which is sensitive towards reduction is protected. Hydrogenation conditions that can be used are those as described for quinolines in Rylander, *Catalytic Hydrogenation in Organic Synthesis*, 1979, 213-230, Academic Press. Hydrogenation of quinolines to tetrahydroquinolines as well as other methods of reduction is described in Hudlicky, *Reductions in Organic Chemistry Second Edition*, 1996, 72-74, American Chemical Society. 6-aminoquinoline has been hydrogenated to 6-aminotetrahydroquinoline with a platinum oxide catalyst in Example 2 of WO 92/05173. The reduction of quinolines to tetrahydroquinolines with sodium borohydride-nickelous chloride is described by Nose and Kudo, *Chem. Pharm. Bull.*, 1984, 32, 2421-2425. The reduction of quinolines to tetrahydroquinolines with sodium borohydride in acidic media is described by Gribble and Heald, *Synthesis*, 1975, 650-652.

Alternatively, when X, X', Y and Y' are not amines the compounds of this invention can be prepared by reversing this sequence. Thus the reduction step would precede the coupling. The coupling would be done as depicted in (IV) and (V).

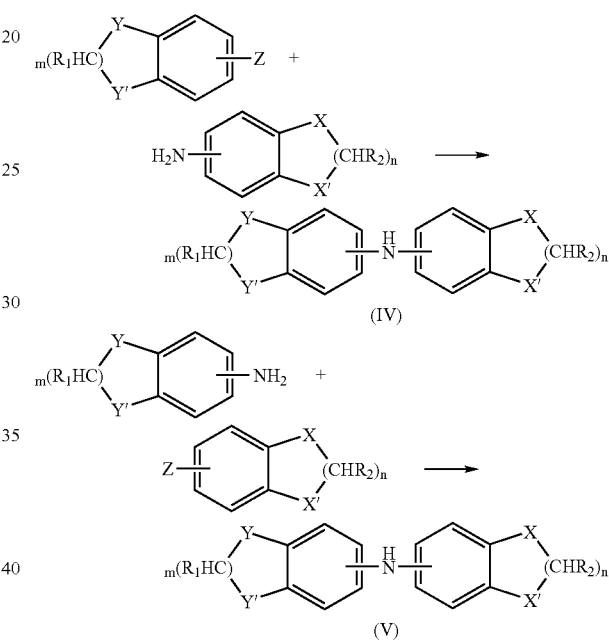

EXAMPLES

The invention is further illustrated by the following examples, which are not to be considered as limitative of its scope. A further understanding of the invention can be had in the following nonlimiting Preparations and Examples. Wherein unless expressly stated in the contrary, all temperatures and temperatures ranges refer to the Centigrade system and the term "ambient" or "room temperature" refers to about 20 to 25° C. The term "percent or %" refers to weight percent, and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r) were determined at 300 mHz, signals are assigned as singlets(s), braod singlets (bs), doublets (d), double doublets (dd), triplets (t), double triplets (dt), quartets (q), and multiplets (m), and cps refers to cycles per second.

Example 1

Preparation of N-(1,2,3,4-tetrahydroquinolin-8-yl)-1,2,3,4-tetrahydroquinolin-8-amine

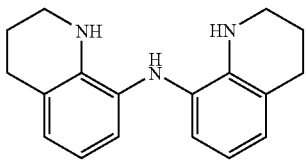

A solution of 1.24 grams of bis(8-quinolinyl)amine (prepared as described in J. C. Peters, S. B. Harkins, S. D. Brown and M. D W. Day, *Inorg. Chem.*, 2001, 40, 5083-5091) in 100 mL of acetic acid containing 0.07 grams of platinum(IV) oxide was hydrogenated at 45 psi for 1.5 hours on a Parr low-pressure hydrogenator. The solution was filtered through diatomaceous earth; concentrated in vacuo; and neutralized with 6N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 1.25 grams of brown oil which was the desired product. $^1$H NMR (CDCl$_3$) δ 6.5-6.75 (m, 6H), 4.8 (bs, 1H), 3.7 (bs, 1H), 3.25 (t, 4H), 2.8 (t, 4H), 1.95 (p, 4H), 1.6 (bs, 1H).

Example 2

Step A—Preparation of N-quinolin-8-ylquinolin-6-amine

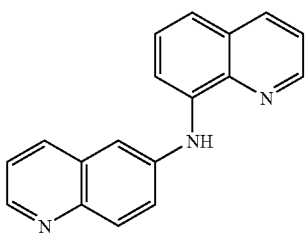

To a flask equipped with a magnetic stirrer, reflux condensor, and nitrogen inlet was added 8-aminoquinoline (4.2 grams, 29.0 mmoles), 6-bromoquinoline (6.0 grams, 29.0 mmoles), tris(dibenzylideneacetone)dipalladium (0) (0.4 grams, 0.48 mmoles), rac-2,2'-bis(diphenylphosphino)-1,1'-binapthyl (0.6 grams, 0.60 mmoles), sodium tert-butoxide (4.7 grams, 49.0 mmoles) and anhydrous toluene (80 mL). The contents of the flask were refluxed for three days; cooled to room temperature; and filtered through a pad of silica gel. The silica gel pad was then eluted with dichloromethane (60 mL) and ethyl acetate (60 mL). The combined organic layers were concentrated in vacuo to yield a yellow solid. The solid was chromatographed on silica gel, eluting with a hexane/ethyl acetate gradient to afford 4.4 grams of the desired product as a yellow solid. $^1$H NMR (CDCl$_3$) δ 8.8 (d, 2H), 8.6 (bs, 1H), 8.0-8.2 (m, 3H), 7.2-7.8 (m, 7H).

Step B—Preparation of N-(1,2,3,4-tetrahydroquinolin-8-yl)-1,2,3,4-tetrahydroquinolin-6-amine

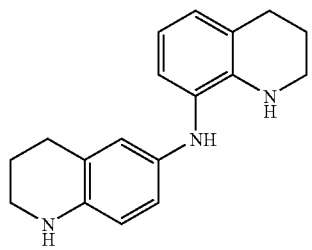

A solution of 3.68 grams of N-quinolin-8-ylquinolin-6-amine from above in 60 mL of acetic acid containing 0.22 grams of platinum(IV) oxide was hydrogenated at 40 psi for 2.0 hours on a Parr low-pressure hydrogenator. The solution was filtered through diatomaceous earth; concentrated in vacuo; and neutralized with 3N aqueous sodium hydroxide. The aqueous phase was diluted with water and extracted three times with ethyl acetate. The combined ethyl acetate layers were washed with brine; dried over anhydrous magnesium sulfate, filtered and concentrated in vacuo to yield 1.6 grams of brown solid. The solid was chromatographed on silica gel, eluting with hexane/ethyl acetate gradient to afford 0.8 grams of the desired product as a purple solid. $^1$H NMR (CDCl$_3$/D$_2$O) δ 6.4-6.9 (m, 6H), 3.2-3.4 (m, 4H), 2.6-2.9 (m, 4H), 1.8-2.1 (m, 4H).

Example 3

Preparation of N-(2,3-dihydro-1-benzofuran-5-yl)-2,3-dihydro-1-benzofuran-5-amine

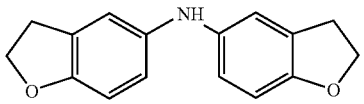

To a flask equipped with a magnetic stirrer, reflux condenser, and nitrogen inlet was added 2,3-dihydro-1-benzofuran-5-amine (4.53 grams, 33.3 mmoles, prepared as in Example 23 of U.S. Pat. No. 20040029932), 5-bromo-2,3-dihydrobenzofuran (6.63 grams, 32.9 mmoles), tris(dibenzylideneacetone)dipalladium (0) (0.61 grams, 0.67 mmoles), rac-2,2'-bis(diphenylphosphino)-1,1'-binapthyl (0.83 grams, 1.33 mmoles), sodium tert-butoxide (6.44 grams, 66.6 mmoles) and anhydrous toluene (60 mL). The contents of the flask were refluxed for three days; cooled to room temperature; and filtered through a pad of silica gel. The silica gel pad was then eluted with dichloromethane (200 mL). The combined organic layers were concentrated in vacuo to yield a dark yellow oil. The solid was chromatographed on silica gel, eluting with a hexane/ethyl acetate gradient. The resulting solid was recrystallized from ethanol to afford 1.8 grams of the desired product as a white solid. $^1$H NMR (CDCl$_3$/D$_2$O) δ 6.55-6.95 (m, 6H), 4.5 (t, 4H), 3.15 (t, 4H).

Example 4

Preparation of N-1,3-benzodioxol-5-yl-1,3-benzodioxol-5-amine

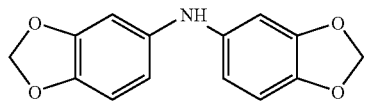

To a flask equipped with a magnetic stirrer, reflux condensor, and nitrogen inlet was added 3,4-(methylenedioxy) aniline (5.34 grams, 38.9 mmoles), 4-bromo-1,2-(methylenedioxy) benzene (6.41 grams, 31.9 mmoles), tris(dibenzylideneacetone)dipalladium (0) (0.71 grams, 0.8 mmoles), 1,1'-bis(diphenylphosphino)-ferrocene (1.29 grams, 2.3 mmoles), sodium tert-butoxide (4.20 grams, 43.7 mmoles) and anhydrous toluene (40 mL). The contents of the flask were heated to 80° C. for three days; cooled to room temperature; and filtered through a pad of silica gel. The silica gel pad was then eluted with dichloromethane (240 mL). The combined organic layers were concentrated in vacuo to yield a dark yellow oil. The oil was chromatographed on silica gel, eluting with a hexane/ethyl acetate gradient to afford 6 grams of yellow solid. The solid was triturated with hexane and filtered to afford 3.9 grams of the desired product as a white solid. $^1$H NMR (CDCl$_3$) δ 6.7 (d, 2H), 6.55 (s, 2H), 6.35 (d, 2H), 5.85 (s, 4H), 5.35 (bs, 1H).

Performance Examples

Oxidation studies of the products of selected Examples were carried out in a bulk oil oxidation bench test as described by E. S. Yamaguchi et al. in Tribology Transactions, Vol. 42(4), 895-901 (1999). In this test the rate of oxygen uptake at constant pressure by a given weight of oil was monitored. The time required (induction time) for rapid oxygen uptake per 25 grams of sample was measured at 171° C. under 1.0 atmosphere of oxygen pressure. The sample was stirred at 1000 revolutions per minute. The results are reported, however, as time for rapid oxygen uptake per 100 grams of sample. The oil contained a catalyst added as oil soluble naphthenates to provide 26 ppm iron, 45 ppm copper, 512 ppm lead, 2.3 ppm manganese, and 24 ppm tin.

The screening formulation contained in a Group 2+ base oil 7.0 mmoles/kg dialkyl zinc dithiophosphate, 4.0% polyisobutenyl succinimide, 0.5% dinonyldiphenylamine, 0.25% polyisobutenyl succinimide (this polyisobutenyl succinimide also contains 5.5 weight percent molybdenum, 48.5 mmoles/kg overbased calcium sulfonate detergent and 0.3% V.I. improver. Oxidation bench test results are presented in Table 1.

TABLE 1

| Performance Example | Sample | Concentration of added Sample (weight percent) | Hr to rapid O$_2$ uptake (0.5 weight percent) |
| --- | --- | --- | --- |
| Base | — | 0 | 14.1 |
| α | Comparative Example A[1] | 0.5% | 32.5 |
| β | Comparative Example A[1] | 1.0% | 41.0 |
| γ | Comparative Example B[2] | 0.5% | 41.9 |
| δ | Comparative Example B[2] | 1.0% | 83.5 |
| ε | Example 1 | 0.5% | 85.0 |
| ζ | Example 1 | 1.0% | 111.0 |
| η | Example 2 | 0.5% | 117.0 |
| θ | Example 3 | 0.5% | 51.5 |
| ι | Example 3 | 1.0% | 94.8 |
| κ | Example 4 | 0.5% | 36.4 |

[1]Irganox ® L57 (diphenylamine alkylated with 2,4,4-trimethylpentene) available commercially from Ciba-Geigy
[2]4-(2-octylamino)diphenylamine available from TCI America The excellent oxidation inhibition performance of Performance Examples ε through κ which contained formulations top treated to the baseline formulation with compounds of Examples 1 through 4, as compared to Performance Examples α and β which were top treated with Comparative Example A, an alkylated diphenylamine, is shown in the table. The perhydro cyclic amines of this invention in Examples 1 and 2 (performance examples ε, ζ and η) perform better than the non cyclic amine of Comparative Example B. The advantages on oxidation inhibition can be seen when constraining the heteroatom into a ring.

What is claimed is:

1. A compound according to formula I:

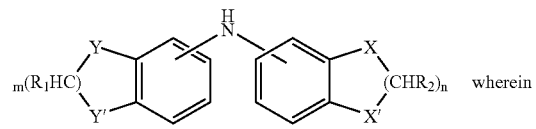

Formula I wherein

R$_1$ and R$_2$ are each independently selected from hydrogen and alkyl from 1 to 20 carbon atoms; X and X' are independently selected from —CHR$_3$—, oxygen, sulfur or NR$_4$, wherein R$_3$ and R$_4$ are independently hydrogen or alkyl from 1 to 6 carbon atoms, with the proviso that at least one of X or X' is a heteroatom positioned ortho or para to the bridging ring nitrogen; and Y and Y' are independently selected from —CHR$_5$—, oxygen, sulfur or NR$_6$ wherein R$_5$ and R$_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

2. The compound according to claim 1, wherein at least one of X and X' is oxygen or NR$_4$, where R$_4$ is hydrogen or alkyl from 1 to 6 carbon atoms.

3. The compound according to claim 2, wherein each R$_2$ is hydrogen.

4. The compound according to claim 2, wherein at least one of X and X' is —CHR$_3$— where R$_3$ is hydrogen or alkyl from 1 to 6 carbon atoms.

5. The compound according to claim 4, wherein R$_3$ is hydrogen.

6. The compound according to claim 2, wherein at least one of Y and Y' are oxygen or NR$_6$, where R$_6$ is hydrogen or alkyl from 1 to 6 carbon atoms.

7. The compound according to claim 6, wherein each $R_1$ is hydrogen.

8. The compound according to claim 6, wherein at least one Y and Y' is —$CHR_5$— where $R_5$ is hydrogen or alkyl from 1 to 6 carbon atoms.

9. The compound according to claim 8, wherein $R_5$ is hydrogen.

10. The compound according to claim 1, wherein m=n.

11. The compound according to claim 10, wherein m is one.

12. The compound according to claim 11, wherein X and Y are oxygen.

13. The compound according to claim 12, wherein X' and Y' are independently selected from oxygen and —$CH_2$—.

14. The compound according to claim 13, wherein X' and Y' are —$CH_2$—.

15. The compound according to claim 1, wherein X and X' are independently selected from —$CHR_3$— and $NR_4$ wherein $R_3$ and $R_4$ are independently hydrogen or alkyl from 1 to 6 carbon atoms.

16. The compound according to claim 15, wherein m=n.

17. The compound according to claim 16, wherein m is two.

18. The compound according to claim 17, wherein Y and Y' are independently selected from —$CHR_5$— and $NR_6$ wherein $R_5$ and $R_6$ are independently hydrogen or alkyl from 1 to 6 carbon atoms.

19. The compound according to claim 18, wherein $R_3$, $R_4$, $R_5$ and $R_6$ are hydrogen.

20. The compound according to claim 1, wherein the compound comprises unsubstituted and alkyl substituted dibenzoperhydroheterocylic amines of Formula I selected from the group consisting of: N-quinolin-8-ylquinolin-6-amine; N-(1,2,3,4-tetrahydroquinolin-8-yl)-1,2,3,4-tetrahydroquinolin-6-amine; N-(2,3-dihydro-1-benzofuran-5-yl)-2,3-dihydro-1-benzofuran-5-amine; N-1,3-benzodioxol-5-yl-1,3-benzodioxol-5-amine and alkyl substituted derivatives thereof.

21. A lubricating oil composition comprising a major amount of an oil of lubricating viscosity and a minor amount of the compound according to formula I:

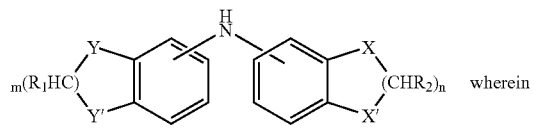

Formula I wherein $R_1$ and $R_2$ are independently selected from hydrogen and alkyl from 1 to 20 carbon atoms; X and X' are independently selected from —$CHR_3$—, oxygen, sulfur or $NR_4$, wherein $R_3$ and $R_4$ are independently hydrogen or alkyl from 1 to 6 carbon atoms, with the proviso that at least one of X or X' is a heteroatom positioned ortho or para to the bridging ring nitrogen; and Y and Y' are independently selected from —$CHR_5$—, oxygen, sulfur or $NR_6$ wherein $R_5$ and $R_6$ are independently hydrogen or alkyl from 1 to 6 carbon atoms; with the proviso that at least one of Y or Y' is a heteroatom positioned ortho or para to the bridging ring nitrogen; and m and n are independently integers from 1 to 2.

22. A lubricating oil composition comprising an oil of lubricating viscosity and a compound according to claim 20.

* * * * *